United States Patent [19]

Sheng

[11] Patent Number: 5,455,294

[45] Date of Patent: Oct. 3, 1995

[54] POLYURETHANE ORTHOPEDIC CAST MATERIAL AND THE METHOD OF ITS PREPARATION

[75] Inventor: Li H. Sheng, 397 Wan Hang Du Lu, Shanghai, China

[73] Assignees: Wang Jian Zhang, Taichung, Taiwan; Li Hai Sheng, Shanghai, China

[21] Appl. No.: 106,337

[22] Filed: Aug. 13, 1993

[30] Foreign Application Priority Data

Aug. 14, 1992 [CN] China .................. 92108533.8

[51] Int. Cl.$^6$ .................. C08J 3/00; C08K 3/00; C08L 75/00; C08G 18/08
[52] U.S. Cl. .................. 524/424; 524/425; 524/589; 524/590; 524/871; 524/875; 528/53; 528/57; 528/60; 528/65; 528/66; 528/73; 528/77; 602/8
[58] Field of Search .................. 524/589, 590, 524/424, 425, 871, 875; 528/53, 57, 60, 65, 66, 73, 77; 602/8

[56] References Cited

U.S. PATENT DOCUMENTS

| | | | |
|---|---|---|---|
| 4,427,002 | 1/1984 | Baron et al. ............ | 128/83 |
| 4,433,680 | 2/1984 | Yoon ............ | 128/90 |
| 4,574,793 | 3/1986 | Lee et al. ............ | 128/90 |
| 4,644,280 | 2/1987 | Paltiel ............ | 324/309 |
| 4,655,208 | 4/1987 | Yoon ............ | 128/156 |
| 4,683,877 | 8/1987 | Ersfeld et al. ............ | 128/90 |
| 4,705,840 | 11/1987 | Buckanin ............ | 528/53 |
| 4,841,958 | 6/1989 | Ersfeld et al. ............ | 128/90 |
| 4,856,502 | 8/1989 | Ersfeld et al. ............ | 128/90 |
| 4,888,225 | 12/1989 | Sandvig et al. ............ | 428/71 |
| 4,893,617 | 1/1990 | Bartial et al. ............ | 128/90 |
| 4,968,542 | 11/1990 | Gasper et al. ............ | 428/71 |
| 4,984,566 | 1/1991 | Sekine et al. ............ | 128/90 |
| 5,005,566 | 4/1991 | Klintworth, Jr. ............ | 128/90 |
| 5,007,418 | 4/1991 | Bartizal et al. ............ | 128/90 |
| 5,027,873 | 7/1991 | Anselm ............ | 144/224 |
| 5,042,464 | 8/1991 | Skwor et al. ............ | 128/80 |
| 5,052,380 | 10/1991 | Polta ............ | 128/90 |
| 5,195,946 | 3/1993 | Li et al. ............ | 602/8 |

FOREIGN PATENT DOCUMENTS

| | | | |
|---|---|---|---|
| 2666743A | 9/1991 | France ............ | 602/8 |
| 88255551 | 4/1990 | Japan . | |
| 40202215 | 4/1990 | Japan ............ | 602/8 |
| 88/02636 | 4/1988 | WIPO . | |
| WO93/04709 | 3/1993 | WIPO . | |

*Primary Examiner*—Paul R. Michl
*Assistant Examiner*—Patrick Niland
*Attorney, Agent, or Firm*—Townsend and Townsend Khourie and Crew

[57] ABSTRACT

The present invention concerns a new, unconventional, mold-binding, water solidified polyurethane cast to be used in orthopedic departments for the correction of deformities, fixation of fractured limbs and joints, and mollification of affected parts, as well as the method of its preparation. The chief constituent, a polyurethane prepolymer, contains a stabilizer that can prolong appreciably the storage period of the cast material, maleic anhydride, and a mixed catalyst for control of hardening time, bis(2-morpholinoethoxy)ethane and anhydrous potassium carbonate.

9 Claims, No Drawings

POLYURETHANE ORTHOPEDIC CAST MATERIAL AND THE METHOD OF ITS PREPARATION

BACKGROUND OF THE INVENTION

This invention involves a new, unconventional, mold-binding cast material to be used in orthopedic departments for the correction of deformities, fixation of fractured limbs and joints, and mollification of affected parts. The material is prepared by coating a stable, water hardening polyurethane prepolymer on a substrate of meshed synthetic or glass side chain fabric, characterized in that the stabilizer in the polyurethane prepolymer is maleic anhydride, and the catalyst is a mixture of bis(2-morpholinoethoxy)ethane and anhydrous potassium carbonate.

In recent years, U.S. Pat. No. 4,376,438 first proposed replacement of plaster casts in fracture treatment with a cast material formed by impregnation of fabric with a water hardening polyurethane prepolymer. Such a cast is used in the same way as the plaster cast, i.e., it is bound up on the patient's limb directly after impregnation with water. The water causes the prepolymer to polymerize, thereby producing a hardening and shaping effect on the relevant part of the patient. Since such cast material has the merits of being lightweight, high strength, fine porosity, water resistance, and X-ray penetrability, as well as convenience in use, it has found extensive application in medical and health institutions in various countries of the world. For the cast to harden quickly in 15 minutes as required clinically, it is necessary to incorporate a proper amount of catalyst in the polyurethane prepolymer. The presence of catalyst in the prepolymer and the invasion of little amount of moisture in the process of cast preparation and packaging may lead to the side reaction of gelatination of polyurethane prepolymer in the cast prior to use, or in the storage period, causing premature hardening of the cast, and thereby making it impossible to use.

To prevent initial hardening of the cast material, and improve the stability of the cast during storage, U.S. Pat. Nos. 4,433,680 and 4,644,280, as well as the Chinese patent 89103603.2, have proposed incorporation of benzoyl chloride into the polyurethane prepolymer as a stabilizing agent. However, benzoyl chloride is a highly corrosive and easily decomposing liquid. Even the addition of a small amount results in an irritating smell in the cast material, so that as a medical raw material, there will be difficulty in its being accepted by medical workers.

U.S. Pat. No. 427,002 proposes use of organic acids, such as phosphoric acid, as the stabilizer. Nevertheless, phosphoric acid mixed into prepolymer is liable to decompose into red phosphate, thus failing to have a stabilizing effect.

Both U.S. Pat. No. 4,574,793 and Chinese patent 90102934.3 have proposed the addition of a small amount of methyl sulfonic acid in the polyurethane prepolymer as a stabilizing agent. However, methyl sulfonic acid is a strong acid; once gaining entrance during preparation of polyurethane prepolymer, it will combine quickly with the OH group in the polyether, and reduce the stability of the prepolymer.

PCT/GB8700716 (W088/02636) proposes use of organic acid anhydrides, such as butanedioic anhydride, as the stabilizer. It is true that addition of it during preparation of polyurethane prepolymer may have a stabilizing effect, but butanedioic anhydride is incorporated in the prepolymer as solid particles by grinding into fine granules smaller than 75 μm. The impossibility of a fairly even distribution affects stabilization of the prepolymer.

SUMMARY OF THE INVENTION

The present invention includes a composition useful for making orthopedic casts to correct deformities, set fractured limbs and joints and mollify affected parts. The present invention also includes methods for preparing the cast material.

In one embodiment the present invention includes an orthopedic cast material comprising a polyurethane prepolymer. The prepolymer includes a maleic anhydride, an aromatic isocyanate, a polyether selected from the group consisting of dihydroxy polyethers, trihydroxy polyethers, and mixtures thereof, and a catalyst comprising potassium carbonate and bis(2-morpholinoethoxy)ethane. The bis(2-morpholinoethoxy)ethane may have the structure shown in formula I, below.

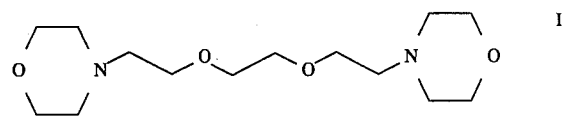

In a particularly preferred embodiment, the prepolymer includes between about 0.1 to 5.0%, more preferably between about 0.5 to 2% a maleic anhydride; an aromatic isocyanate; a polyether selected from the group consisting of dihydroxy polyethers, trihydroxy polyethers and mixtures thereof, where the isocyanate and the polyether are present in a quantity sufficient to achieve a NCO:OH ratio of between about 3:1 to 9:1, more preferably about 3:1, to 6:1; and a catalyst comprising potassium carbonate granules having an average diameter less than about 100 μm, said potassium carbonate being present in an amount between about 1.0 and 10.0%, more preferably between about 4 and 6.0% of said polyurethane prepolymer, by weight, and bis(2-morpholinoethoxy)ethane, where the bis(2-morpholinoethoxy)ethane has the structure shown in formula I, above. The NCO content of the prepolymer may range from about 0 to about 15%. The bis(2-morpholinoethoxy)ethane may be present in an amount of about 0.1% to 10.1%, more preferably about 0.5% <xo about 2%, by weight, of the prepolymer. The potassium carbonate may range from about 1% to 10%, more preferably from about 4% to about 6%, by weight, of the prepolymer.

In still yet another aspect, the present invention includes a method of preparing an orthopedic cast material. The method involves combining the following components under a substantially nitrogen atmosphere to form a polyurethane prepolymer:

(i) a polyether selected from the group consisting of dihydroxy polyethers, trihydroxy polyethers and mixtures thereof;

(ii) an aromatic isocyanate, said aromatic isocyanate being present in an amount such that the NCO:OH ratio is between about 3:1 to 9:1, more preferably between about 3:1 and 6:1;

(iii) antifoam silicon oil;

(iv) maleic anhydride in an amount between about 0.1 to 5.0%, more preferably between about 0.5% to 2.0%, of the total weight of the prepolymer;

(v) bis(2-morpholinoethoxy)ethane in an amount between about 0.1 to 10.1%, more preferably between about 0.5

% to 2%, of said prepolymer by weight; and (vi) anhydrous potassium carbonate, the amount of said carbonate being between about 1.0 and 10.0%, more preferably between about 4% to 6%, of said prepolymer by weight. The method may further comprise the steps of coating the material on a substrate in a substantially anhydrous nitrogen atmosphere and mixing the components until they are distributed substantially evenly throughout the mixture. The substrate may comprise a meshed side chain fabric having good air permeability. Preferred substrates include porous synthetic or glass fibers woven in a side chain weft. Particularly preferred is a meshed dacron substrate.

The orthopedic cast materials of the present invention cure rapidly upon exposure to water and yet provide an exceptionally stable and long shelf-life. These and other advantages of the present invention will become apparent upon reading the Detailed Description of the Preferred Embodiments below.

DETAILED DESCRIPTION OF THE PREFERRED EMBODIMENTS

Without wishing to be bound by any particular theory of action, the present invention proposes use of maleic anhydride as a stabilizing agent, because maleic anhydride can react with moisture and water soluble alkaline group in the prepolymer, giving rise to a derivative of acidic maleic acid after reaction with the gel formed by a small amount of isocyanic acid radical in the prepolymer. The prepolymer in such an acid environment serves to prevent effectively premature hardening of orthopedic cast material prior to use, or during storage period. As maleic anhydride is soluble in such solvents as chlorobutanol and ether, the maleic anhydride is evenly scattered in the prepolymer in the form of solution during preparation of polyurethane prepolymer, which serves to stabilize the prepolymer adequately, overcome the shortcomings arising from presence of other stabilizers, and improve appreciably the storing stability of the orthopedic cast.

The content of the maleic anhydride stabilizer is 0.1 to 5.0% of polyurethane prepolymer, the preferred content being 0.5 to 2.0%.

The mixed catalyst used in the invention includes two parts, liquid and solid phase, of which the liquid phase catalyst is a kind of new compound of double morpholine structure prepared by the synthesis of dichlorodiethoxyethane and morpholine, i.e., bis(2-morpholinoethoxy-)ethane; the synthetic reaction formula is as follows:

volatile transparent viscous liquid; readily soluble in water and such organic solvents as benzine, toluene, acetone, chloroform, ethyl acetate, and ether. The formation rate of side reaction resulting from use of such a morpholine compound as a catalyst of polyurethane prepolymers is much lower than those of other traditional tertiary amine catalysts. While ensuring the clinically required hardening time, there is a manifest improvement in the storing stability of the cast.

The amount of catalyst is preferably 0.1 to 10.1% of the total weight of the polyurethane prepolymer, a more preferred amount being 0.5 to 2.0%.

The solid phase catalyst is formed of anhydrous potassium carbonate, which is ground into fine granules under 100 μm to be scattered throughout the polyurethane prepolymer. As this compound is not soluble in polyurethane prepolymer, it is quite stable in the prepolymer before use; during usage, once the cast encounters water, the potassium carbonate is immediately dissolved in water to become alkaline catalyst solution, causing the cast to harden quickly.

The amount of anhydrous potassium carbonate preferably is 1 to 10% of the total weight of polyurethane prepolymer. A more preferred amount is 4 to 6%.

The aromatic isocyanate in the polyurethane prepolymer of the invention can be any one of the aromatic isocyanates commonly known in the polyurethane chemistry, such as the compound, described in the book "Polyurethane Chemistry and Technology" published by Interscience Publishing House in 1962.

The aromatic isocyanates include toluene diisocyanate (TDI), diphenylmethane diisocyanate (MDI), or modified solution MDI containing carbodiimide group.

The polyhydroxy compound in the polyurethane prepolymer of the invention is a dihydroxy polyether or a mixture of a dihydroxy polyether a and trihydroxy polyether, with a molecular weight of 300 to 1500. The ratio of isocyanate (NCO) to hydroxyl (OH) in the polyurethane prepolymer preferably is 3:1 to 9:1, with the NCO content in the range of 0 to 15% more preferably.

The preparation of polyurethane orthopedic cast involved in the invention is carried out in a substantially controlled dry $N_2$ environment with low humidity. The water content in the system is preferably lower than 50 PPm. After the processes of cloth delivery, coating, rolling, cutting and sealing, a given quantity of polyurethane prepolymer is coated on the substrate under appropriate temperature. Then it is hermetically sealed in a composite aluminum-plastics bag under $N_2$ protection. For a cast of 4" width, the prepolymer coating amount will be 18 g/m. The low humidity,

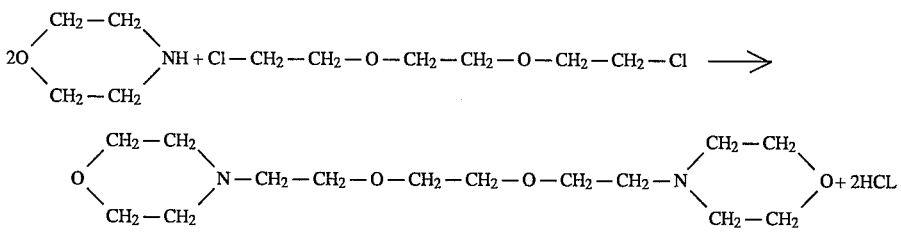

Molecular formula: $C_{14}H_{28}N_2O_4$

Molecular weight: 288

Boiling range: 145°–150° C./1–2 mm Hg

Physical characteristics: Colorless, tasteless, atoxic, nondry $N_2$ system includes: air compressor, cryogenic separator, drying column, regenerative tower, and complete sets of automatic meters and monitoring instruments. Preferably, the air is highly compressed and separated into 99.999% content of pure $N_2$, which is then desiccated to a greatdegree, after which the water content in $N_2$ may reach less than 50 PPm.

The material of the orthopedic cast of the invention is formed preferably of meshed side chain fabric having good air permeability, with porous synthetic or glass fibers used as substrate, woven by means of 1×3 side chain weft. Typically, such fabric may be found in 4 widths: 2" (5.0 cm), 3" (7.5 cm), 4" (10.0 cm), and 5" (12.5 cm), each square centimeter containing 15 to 30 meshes; and it has a thickness of 0.01 to 0.05 centimeters.

The packing material for the cast has a direct effect on its storing stability. The orthopedic cast of the present invention makes use of PET/AL/LDPE. EVA multi-layer co-extruded, composite aluminum/plastics, 3-side-sealed soft packaging bags. Such a composite packaging bag has the features of a metal container in terms of storage and durability. At the same time, the different layers of films forming the composite material have their own merits, such as high degree of air-tightness, being well proof against moisture and corrosion, as well as tolerating high temperature and high tension. Hence it is particularly suitable for use as packaging bag for long-term storage of orthopedic casts.

The storage period of the orthopedic cast is an important indicator of the stability of the polyurethane prepolymer, which depends largely upon its chemical structure and the dissociation energy of the chain. Since polyurethane prepolymer is not a single homopolymer, raising the storing temperature i in effect increases the dissociation energy of the chain, stimulating thermal response, and accelerating solidification. The thermal aging quick test approach constitutes an effective evaluation method for appraising the stability, term of usage, and storage period of the polyurethane material. To date, however, there has been no uniform, standard test method internationally, with consequent enormous differences in test temperatures and conditions: Normally the selected test temperature exceeds the actual working temperature by 20° to 40° C. For the polyurethane cast of the present invention, 40° C. is selected as the temperature for the thermal aging test. Storage under this temperature for 124 days without hardening is tantamount to the possibility of storing for a period of two years in 20° C. room temperature.

In the following some embodiments of the invention are given.

1. Preparation of polyurethane prepolymer

| | |
|---|---|
| Formula: Dihydroxy polyether Pluracol 710, OH = 150, (BASF Company) | 6410 g |
| Liquid MDI Lupranate ® MM-103, (BASF Company) NCO:OH = 4.2:1 | 3580 g |
| Antifoam silicon oil | 20 g |
| Maleic anhydride | 100 g |
| bis(2-morpholinoethoxy)ethane | 80 g |
| Anhydrous potassium carbonate | 500 g |

In a 10 cubic liter reactor equipped respectively with thermometer, mixer, liquid supplier, and $N_2$ inlet, dihydroxy polyether, antifoam silicon oil, and maleic anhydride acetone solution are first added according to the formula, and pre-mixed until uniform. Then it is heated until it reaches a temperature of 55° C., while liquid MDI is added in droplets within 30 minutes, with the temperature controlled at 60° C. After reaction for 1.5 hours, the mixed catalyst bis(2-morpholinoethoxy)ethane, and less than 100 μm of anhydrous potassium carbonate are successively added. After stirring and mixing for 10 minutes, it is cooled to 40° C., then withdrawn under $N_2$ protection and placed in a container ready for use. The characteristic viscosity of the prepolymer is 2500 cP at 50° C., and the NCO content is 13.9%.

2. Preparation of polyurethane orthopedic cast

Take 5000 g of polyurethane prepolymer prepared as above and heat it to 50° C. Under low humidity, dry $N_2$ environment with water content less than 50 PPm, following the processes of cloth delivery, coating, rolling, cutting and sealing, the prepolymer is coated on the meshed dacron substrate using double roller coating method. Then it is heat-sealed and packed in the aluminum/plastics composite bag. Each roll is 4 inches wide and 3.6 m long. The coating amount is 18 g/m, and air permeability 510 l/m/sec for an 8-layered cast. The compression strength as measured with Instron 1122 model testing machine, with a speed of 100 mm/min, is 160 N for an 8-layer cast. After immersion in water for 5 days in 20° C. room temperature, the strength of the cast does not change. The cast to be used after unpacking should be immersed in 25° C. water for 15 seconds before winding round the affected part of the patient, with a hardening time of 8 minutes. The accelerated thermal aging test conducted by placing the cast material in a temperature of 40° C., and its storage for 192 days without any hardening signifies that it can be stored for a period of over 3 years under 20° C. room temperature.

Although the foregoing invention has been described in some detail by way of illustration and example, for purposes of clarity of understanding, it will be obvious that certain changes and modifications may be practiced within the scope of the appended claims.

What is claimed is:

1. An orthopedic cast material comprising a polyurethane prepolymer, said prepolymer comprising:
   (a) a maleic anhydride;
   (b) an aromatic isocyanate;
   (c) a polyether selected from the group consisting of dihydroxy polyethers, trihydroxy polyethers, and mixtures thereof; and
   (d) a catalyst comprising potassium carbonate and bis(2-morpholinoethoxy)ethane, said bis(2-morpholinoethoxy)ethane having the structural formula shown below:

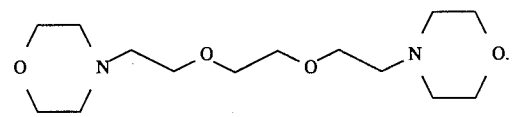

2. The orthopedic cast material as described in claim 1, wherein the weight of said maleic anhydride is between about 0.1 and 5.0% of the total weight of said polyurethane prepolymer.

3. The orthopedic cast material as described in claim 1, wherein the weight of said bis(2-morpholinoethoxy)ethane is between about 0.1 and 10.1% of the total weight of polyurethane prepolymer.

4. The orthopedic cast material as described in claim 1, wherein said potassium carbonate is anhydrous potassium carbonate ground into granules having an average diameter of less than about 100 μm, and the weight of said anhydrous potassium carbonate in said material is between about 1 and 10% of the total weight of said polyurethane prepolymer.

5. The orthopedic cast material as described in claim 1, wherein said isocyanate is diphenylmethane-4,4'-diisocyanate, and an amount of said polyhydroxy compound is added to create a NCO:OH ratio of between about 3:1 to 6:1.

6. The material of claim 5, wherein said polyhydroxy compound is a mixture of di- and trihydroxy polyethers.

7. An orthopedic cast material comprising a polyurethane prepolymer, said prepolymer comprising:
   (a) a maleic anhydride present in an amount between about 0.1 to 5.0%, by weight, of said polyurethane prepolymer;
   (b) an aromatic isocyanate;
   (c) a polyether selected from the group consisting of dihydroxy polyethers, trihydroxy polyethers and mixtures thereof, wherein said isocyanate and said polyether are present in a quantity sufficient to achieve a NCO:OH ratio of between about 3:1 to 6:1; and
   (d) a catalyst comprising potassium carbonate granules having an average diameter less than about 100 µm, said potassium Carbonate being present in an amount between about 1.0 and 10.0% of said polyurethane prepolymer, by weight, and bis(2-morpholinoethoxy)ethane, said bis(2-morpholinoethoxy)ethane having the structural formula shown below:

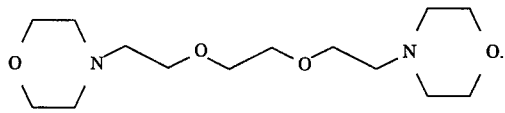

8. A method of preparing an orthopedic cast material, said method comprising combining the following components under a substantially nitrogen atmosphere to form a polyurethane prepolymer:

(i) a polyether selected from the group consisting of dihydroxy polyethers, trihydroxy polyethers and mixtures thereof;

(ii) an aromatic isocyanate, said aromatic isocyanate being present in an amount such that the NCO:OH ratio is between about 3:1 to 6:1;

(iii) antifoam silicon oil;

(iv) maleic anhydride in an amount between about 0.1 to 5.0% of the total weight of said prepolymer;

(v) bis(2-morpholinoethoxy)ethane in an amount between about 0.1 to 10.1% of said prepolymer by weight; and (vi) anhydrous potassium carbonate, the amount of said carbonate being between about 1.0 and 10.0% of said prepolymer by weight.

9. The method of claim 8, further comprising the steps of coating said material on a substrate in a substantially anhydrous nitrogen atmosphere and mixing said components until they are distributed substantially evenly throughout said mixture.

* * * * *